United States Patent [19]

Sadoun et al.

[11] Patent Number: 5,011,403
[45] Date of Patent: Apr. 30, 1991

[54] ORTHODONTIC BRACKET MADE FROM ZIRCONIUM OXIDE

[76] Inventors: Michael Sadoun, 3 avenue Séverine, 92400 Courbevoie; Alain Decker, 113, avenue Gabriel Péri, 91700 Ste Genevieve des Bois, both of France

[21] Appl. No.: 311,913

[22] Filed: Feb. 17, 1989

[30] Foreign Application Priority Data

Feb. 19, 1988 [FR] France ................................. 8802017

[51] Int. Cl.$^5$ .............................................. A61C 3/00
[52] U.S. Cl. ............................................ 433/8; 433/9
[58] Field of Search ................. 433/8, 9, 201.1, 222.1, 433/228.1

[56] References Cited

U.S. PATENT DOCUMENTS

| 4,407,984 | 10/1983 | Ratcliffe et al. | 433/228.1 |
| 4,503,169 | 3/1985 | Randkler | 433/222.1 |
| 4,902,224 | 2/1990 | Colins et al. | 433/8 |
| 4,915,625 | 4/1990 | Tsukuma et al. | 433/8 |

Primary Examiner—John J. Wilson
Attorney, Agent, or Firm—Cushman, Darby & Cushman

[57] ABSTRACT

A nonporous ceramic bracket for bonding to the external face of a tooth is made of compressed zirconium oxide particles which are partially stabilized by a transition metal oxide. The bracket has a color and translucency substantially corresponding to the tooth to which it is bonded.

14 Claims, 1 Drawing Sheet

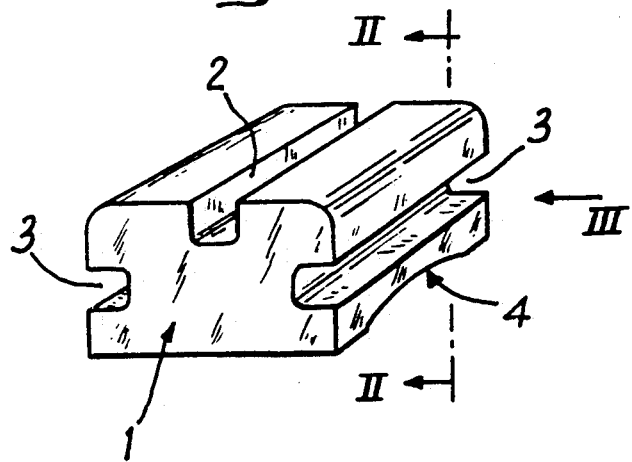
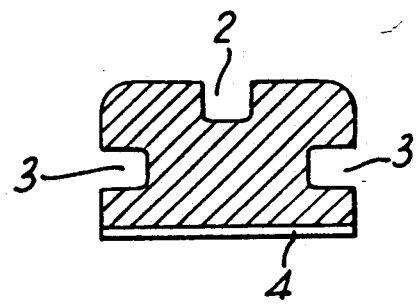
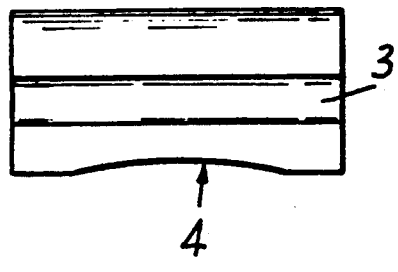
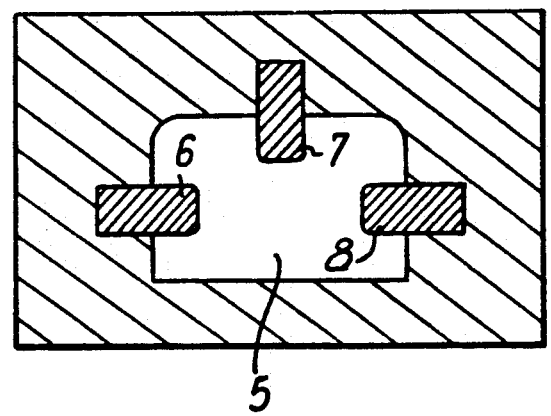

ORTHODONTIC BRACKET MADE FROM ZIRCONIUM OXIDE

FIELD OF THE INVENTION

The present invention relates to a novel device for fixing orthodontic archwires and its method of manufacture.

BACKGROUND OF THE INVENTION

It is known that orthodontia currently uses devices known as brackets, which are bonded to the external face of the teeth and are integrally joined by a metal wire that exerts elastic strains, making it possible to adjust the relative positions of the teeth involved.

Such brackets are at present made of stainless steel or of a nickel/chromium alloy, which makes them unattractive because they are quite visible when they are applied to the teeth.

It is also known to make these brackets with the aid of transparent plastic materials, but these materials chemically degrade after a very short period of use, and do not have sufficient mechanical rigidity.

It has also been proposed that brackets be made of sintered alumina, but such brackets are fragile and have a high production cost.

OBJECT AND SUMMARY OF THE INVENTION

The present invention relates to brackets that are easy to make economically, that have excellent mechanical qualities, in particular as to their strength, and the appearance of which, in particular in terms of color and translucency, is equivalent to that of the teeth to which they are to be bonded.

The subject of the present invention is a ceramic bracket, characterized in that it is made of zirconium oxide, partially stabilized by the addition of oxides of transition metals and sintered; that it is not porous; and that it has a color and a translucency substantially corresponding to the color and translucency of the teeth.

In a preferred embodiment, the particle size of the ceramic is less than 0.5 microns, for example being included between 0.2 and 0.5 microns.

According to the invention, it is also advantageous that in addition to the above-mentioned additives, the zirconium oxide contains less than 0.01% by weight of impurities.

The subject of the present invention is also a method for manufacturing brackets, characterized in that a powder of partially stabilized zirconium oxide (zirconia) is prepared; the partially stabilized zirconium oxide powder is atomized to obtain pellets of particles; a water-soluble organic binder and one or more oxides of transition metals are added, in proportions corresponding to the color and degree of translucency that it is desired to lend to the bracket; that the thus-obtained mixture is molded by pressure to obtain a crude blank; optionally, this crude blank is machined to lend it its definitive shape and/or surface state; and the blank is subjected to sintering.

According to the invention, a pure zirconium oxide powder that contains less than 0.01% of impurities is preferably used.

According to the invention, the zirconium oxide ($ZrO_2$) is for example partially stabilized by the addition of small proportions of oxide.

To this end, it is for instance possible to add approximately 3 to 8% and preferably 3 to 5% of yttrium oxide ($Y_2O_3$), from 3 to 10% and preferably 3 to 5% of calcium oxide (CaO), 8 to 15% and preferably 8 to 10% of magnesium oxide (MgO), or 11 to 20% and preferably 14 to 17% cerium oxide ($CeO_2$) to the zirconia, all these percentages being given by weight.

The zirconium oxide thus partially stabilized is in the form of a powder the granulometry of which is advantageously between 0.02 and 1 micron and preferably between 0.1 and 1 micron.

According to the invention, a pelletization of the partially stabilized zirconium oxide particles is then performed, so that by a standard atomization technique, pellets having a preferably substantially spherical form are obtained. These particle pellets have a diameter of between 50 and 200 microns, for instance, and preferably between 80 and 100 microns.

According to the invention, the partially stabilized zirconium oxide powder is mixed with a water-soluble organic binder in a proportion between 0.5 and 5% by weight of binder, for example, and then atomized.

A thermoplastic binder, such as a polyvinyl alcohol, a wax, an acrylic resin, or dextrin, can advantageously be used.

According to the invention, one or more oxides of transition metals, such as iron oxide, manganese oxide, or nickel oxide, is also incorporated into the mixture.

The selection and proportions of the various oxides used is done as a function of the coloration it is desired to lend to the bracket made in accordance with the invention, and as a function of the degree of translucency desired to be obtained.

These metal oxides may be incorporated either in powdered form or in the form of water-soluble salts that are put in solution prior to atomization of the powder and which, after calcination, free the corresponding oxide at the time of the sintering. This latter method has the advantage of enabling good distribution of the oxides, homogeneity of color and rapidity of reaction.

Hence, hydrated iron sulfate $Fe(SO_4), 7H_2O$, in a proportion of 0.02% to 0.5% by weight of zirconium oxide, for example, or hydrated manganese sulfate $Mn(SO_4), H_2O$, in a proportion of 0.001% to 0.03% by weight of zirconium oxide, for example, or nickel sulfate $Ni(SO_4), 6H_2O$, in a proportion of 0.02% to 0.5% by weight of zirconium oxide, for example, is used.

According to the invention, the blank is preferably obtained by uniaxial compression in a mold, made for example of tungsten carbide, the direction of compression being in the direction of grooves made on the bracket to position the metal wire and retain the fasteners for the wire on the bracket.

This compression may advantageously be attained with pressures on the order of 750 to 3000 $Kg/cm^2$, which makes it possible to obtain crude blanks the density of which varies from approximately 2.5 to more than 3.5 grams per cubic centimeter.

To effect the compression of the crude blank, the mixture containing the plasticizer is preferably brought beforehand to a temperature of approximately 80 to 130° C., which facilitates the operation.

According to the invention, the machining that can be done on the crude blank has the primary objective of attaining the curvature of the face of the bracket intended to be bonded to the teeth.

This machining is done for example along a cylindrical surface having a radius of 20 to 30 mm, for example, preferably with the aid of a diamond grinding wheel with coarse particles (for example from 200 to 500 microns in size), in such a manner as to obtain a rough surface state, to promote the bonding of the bracket to the teeth.

The machining of the crude blank can also involve deburring and rounding off of the angles of the blank with the aid of a fine grinding wheel.

According to the invention, the sintering is effected, preferably in air, at a temperature between approximately 1300° C. and 1650° C. and preferably between 1300 and 1400° C., for a period of approximately 2 to 5 hours for example, and preferably 2 to 3 hours.

The heating to the temperature for sintering can be done with a rate of temperature rise of 5° to 10° per minute, for example.

The bracket thus obtained is then brought progressively to ambient temperature, for example over a period of time of approximately 20 to 60 minutes.

The sintering is advantageously performed such as to obtain a ceramic the particle size of which is less than 1 micron and preferably is between 0.2 and 0.3 microns.

The slot made on the top of the bracket must have dimensions that correspond to those of the metal archwire that is to be fixed on the bracket.

Archwires currently used are for example metal wires having a cross section of 0.56±0.02 mm.

In the case where these tolerances are not adhered to, then the slot in the bracket is finish-ground with the aid of a diamond grinding wheel.

The invention will be better understood from the ensuing description, given by way of example and in no way intended to be limiting, of an embodiment shown in the accompanying drawings.

BRIEF DESCRIPTION OF THE DRAWINGS

FIG. 1 is a perspective view of a bracket according to the invention;

FIG. 2 is a sectional view taken along the line II—II in FIG. 1;

FIG. 3 is an elevation view in the direction of the arrow III—III of FIG. 1; and FIG. 4 is a schematic view of the mold for pressing the crude blank.

DESCRIPTION OF THE PREFERRED EMBODIMENT

FIGS. 1, 2 and 3 show a bracket 1, made according to the invention, which is an element of small dimensions, for example having a thickness of approximately 2.3 mm, a length of approximately 3.5 mm and a width of approximately 2.8 mm.

The bracket 1 has an upper slot 2 intended to receive the archwire that holds the teeth by being fixed to the bracket with the aid of fine metal wires that engage the longitudinal lateral grooves 3 following the contour of the metal archwire located in the slot 2 to hold it there.

The inside face of the bracket is machined in accordance with a preferred embodiment of the invention with a concave cylindrical shape 4, so as to be bonded to the external surface of the tooth.

The cylindrical surface 4 that may have a radius of approximately 25 mm is made in such a manner as to have a certain roughness, which improves the quality of bonding to the tooth.

FIG. 4 is a schematic view showing the matrix in which the crude blank can be compressed. This matrix includes a cavity 5 the general shape of which corresponds to that of the cross section of the bracket. Three detachable pins 6, 7 and 8 project to the inside of the cavity 5, to form the slot 2 and the grooves 3.

The compression of the blank is effected in a direction perpendicular to the plane of FIG. 4.

EXAMPLE 1

For making a bracket according to the invention, the procedure may be as follows:

One begins with a powder of zirconium oxide having a mean granulometry of approximately 0.8 microns and rate of impurities of the metallic type of less than 0.01%.

This zirconium oxide is partially stabilized by the addition of a proportion of 5% by weight of yttrium oxide.

Approximately 1% by weight of a binder comprising a polyvinyl alcohol is added.

0.03% by weight of $Fe(SO_4)$, $7H_2O$ and 0.02% by weight of $Ni(SO_4)$, $6H_2O$ are also added to the mixture to lend the bracket a coloration and translucency corresponding to those of a tooth.

Next, the particles of partially stabilized zirconium oxide powder are atomized, to obtain substantially spherical pellets that have a diameter of approximately 80 microns. Next, the crude blank is molded by compression in a mold, such as that shown in FIG. 4, at a pressure of approximately 800 $Kg/cm^2$, which makes it possible to obtain a crude blank having a density of approximately 2.7 $g/cm^3$.

After that, deburring of the blank and rounding off of the angles of the terminal faces are performed, and the recess 4 shown in FIGS. 1, 2 and 3 is machined with the aid of a diamond grinding wheel, which has particles of approximately 300 microns in size.

Next, sintering in air of the crude blank is performed by introducing it into an oven, which is brought to the temperature of 1400° C., at a rate of 5° per minute.

The blank is kept at this temperature for approximately 2 hours, after which it is allowed to cool in the oven.

Finally, the dimensions of the bracket are checked and it is finish-ground as needed.

EXAMPLE 2

In a variant, a zirconium oxide that is partially stabilized with an addition of 10% of mangesium oxide by weight or 9% of calcium oxide by weight is used, and the granulometry of the thus partially stabilized zirconia powder equals approximately one micron.

Next, 0.02% by weight of hydrated iron acetate $(Fe(C_2H_3O_2)_2, 4H_2O)$, 0.002% by weight of hydrated manganese acetate $(Mn(C_2H_3O_2)_2, 4H_2O)$, and 0.03% by weight of hydrated nickel acetate $(Ni(C_2H_3O_2)_2, 4H_2O)$, is incorporated, to obtain the desired appearance. 5% by weight of acrylic resin is added as a binder.

This powder is pelletized by atomization, to obtain substantially spherical pellets of approximately 200 microns in diameter.

The molding of the blank is performed with a pressure of approximately 300 $Kg/cm^2$, which makes it possible to obtain a density of approximately 3.4 $g/cm^3$.

Sintering is done in air by raising the temperature of the oven at a rate of 10° per minute up to 1550° C., and this temperature is maintained for approximately 4 hours, after which the bracket is allowed to cool and then is checked and finish-ground as needed.

EXAMPLE 3

One begins with a zirconium oxide powder partially stabilized with 16% by weight of cerium oxide ($CeO_2$), which has a granulometry of approximately 0.3 microns.

Approximately 1% by weight of a polyvinyl-alcohol-based binder is added.

To lend the bracket its coloration and translucency, 0.01% by weight of heptahydrated iron sulfate ($Fe(SO_4), 7H_2O$), 0.03% by weight of hexahydrated nickel sulfate ($Ni(SO_4), 6H_2O$), and 0.01% by weight of heptahydrated manganese sulfate ($Mn(SO_4), 7H_2O$) is added to the mixture. Next, atomization is done, in such a manner as to produce substantially spherical pellets having a diameter of approximately 150 microns.

Then, molding of the crude blank is performed at a pressure of approximately 2000 $Kg/cm^2$, which makes it possible to obtain a blank having a density of approximately 3.1 $g/cm^3$.

After having proceeded to the finishing of the blank, sintering is performed by bringing the blank from ambient temperature to 700° C. at a rate of 2° C. per minute. Next, it is brought to 1600° C. at a rate of 5° C. per minute, and kept at the temperature of 1600° C. for 3 hours.

After cooling, finish-grinding of the base of the blank is performed with a diamond grinding wheel having a particle size of approximately 200 microns.

It will be understood that the above examples are given solely by way of example, and that they may be modified in any desirable way without departing from the scope of the invention.

What is claimed is:

1. A nonporous ceramic bracket for bonding to the external face of a tooth consisting essentially of sintered small zirconium oxide particles partially stabilized by a transition metal oxide, said bracket having a color and translucency substantially corresponding to those of said tooth.

2. The nonporous bracket of claim 1 wherein the size of said zirconium oxide particles is less than 0.5 micron.

3. The nonporous ceramic bracket of claim 2 wherein the size of said zirconium oxide particles ranges from 0.2 to 0.5 micron.

4. The nonporous ceramic bracket of claim 1 containing at least 99.99% of said zirconium oxide partially stabilized by a transition metal oxide.

5. The nonporous ceramic bracket of claim 1 wherein said transition metal oxide is yttrium oxide present in an amount ranging from 3 to 8 percent by weight of the weight of zirconium oxide.

6. The nonporous ceramic bracket of claim 5 wherein said yttrium oxide is present in an amount ranging from 3 to 5 percent by weight of the weight of zirconium oxide.

7. The nonporous ceramic bracket of claim 1 wherein said transition metal oxide is calcium oxide present in an amount ranging from 3 to 10 percent by weight of the weight of zirconium oxide.

8. The nonporous ceramic bracket of claim 7 wherein said calcium oxide is present in an amount ranging from 3 to 5 percent by weight of the weight of zirconium oxide.

9. The nonporous ceramic bracket of claim 1 wherein said transition metal oxide is magnesium oxide present in an amount ranging from 8 to 15 percent by weight of the weight of zirconium oxide.

10. The nonporous ceramic bracket of claim 9 wherein said magnesium oxide is present in an amount ranging from 8 to 10 percent by weight of the weight of zirconium oxide.

11. The nonporous ceramic bracket of claim 1 wherein said transition metal oxide is cerium oxide present in an amount ranging from 11 to 20 percent by weight of the weight of zirconium oxide.

12. The nonporous ceramic bracket of claim 11 wherein said cerium oxide is present in an amount ranging from 14 to 17 percent by weight of the weight of zirconium oxide.

13. The nonporous ceramic bracket of claim 1 wherein said bracket has been sintered at a temperature ranging from approximately 1300° to 1650° C.

14. The nonporous ceramic bracket of claim 13 wherein said bracket has been sintered at a temperature ranging from approximately 1300° to 1400° C.

* * * * *

REEXAMINATION CERTIFICATE (2713th)
United States Patent [19]
Sadoun et al.

[11] B1 5,011,403
[45] Certificate Issued Oct. 31, 1995

[54] ORTHODONTIC BRACKET MADE FROM ZIRCONIUM OXIDE

[76] Inventors: Michael Sadoun, 3 avenue Séverine, 92400 Courbevoie; Alain Decker, 113, avenue Gabriel Péri, 91700 Ste Genevieve des Bois, both of France

Reexamination Request:
No. 90/003,469, Jun. 20, 1994

Reexamination Certificate for:
Patent No.: 5,011,403
Issued: Apr. 30, 1991
Appl. No.: 311,913
Filed: Feb. 17, 1989

[30] Foreign Application Priority Data

Feb. 19, 1988 [FR] France .................. 88 02017

[51] Int. Cl.⁶ .................................................. A61C 3/00
[52] U.S. Cl. .................................................. 433/8; 433/9
[58] Field of Search ................. 433/8, 9, 201.1, 433/222.1, 228.1

[56] References Cited

FOREIGN PATENT DOCUMENTS 0218853  4/1987  European Pat. Off. .
2559059  8/1985  France .

OTHER PUBLICATIONS

English translation of French Patent 2559059.

Gupta, T. K., et al., "Effect of stress–induced phase transformation on the properties of polycrystalline zirconia containing metastable tetragonal phase", *Journal of Materials Science 13* pp. 1464–1470 (1978).

*Primary Examiner*—Nicholas D. Lucchesi

[57] ABSTRACT

A nonporous ceramic bracket for bonding to the external face of a tooth is made of compressed zirconium oxide particles which are partially stabilized by a transition metal oxide. The bracket has a color and translucency substantially corresponding to the tooth to which it is bonded.

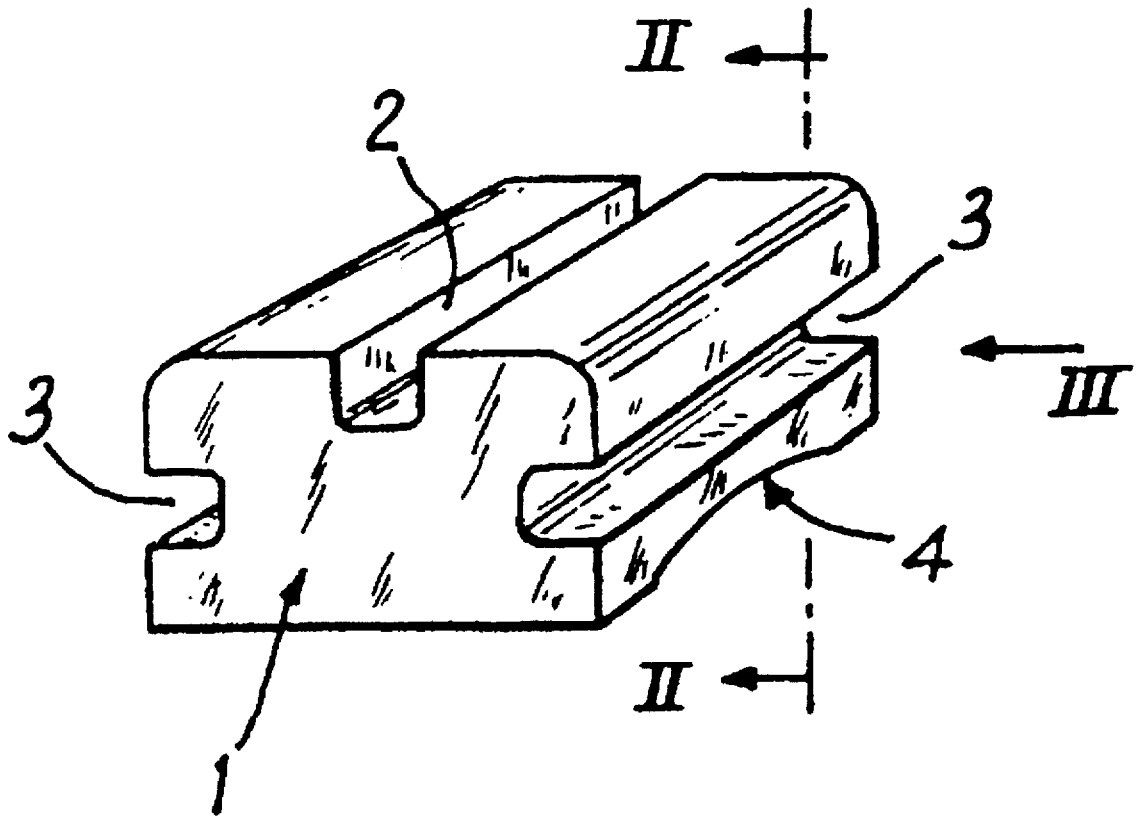

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–14 are cancelled.

* * * * *